United States Patent
Ries et al.

(10) Patent No.: US 12,171,668 B2
(45) Date of Patent: Dec. 24, 2024

(54) INTERVERTEBRAL IMPLANT

(71) Applicant: Joimax GmbH, Karlsruhe (DE)

(72) Inventors: Wolfgang Ries, Linkenheim (DE);
Clemens Barthold, Karlsruhe (DE);
Tobias Scheinost, Karlsruhe (DE)

(73) Assignee: Joimax GmbH, Karlsruhe (DE)

( * ) Notice: Subject to any disclaimer, the term of this patent is extended or adjusted under 35 U.S.C. 154(b) by 232 days.

(21) Appl. No.: 17/869,505

(22) Filed: Jul. 20, 2022

(65) Prior Publication Data

US 2022/0395379 A1 Dec. 15, 2022

Related U.S. Application Data

(63) Continuation of application No. PCT/EP2021/050788, filed on Jan. 15, 2021.

(30) Foreign Application Priority Data

Jan. 21, 2020 (DE) ..................... 10 2020 000 319.2

(51) Int. Cl.
*A61F 2/44* (2006.01)
*A61F 2/30* (2006.01)

(52) U.S. Cl.
CPC ...... *A61F 2/44* (2013.01); *A61F 2002/30108* (2013.01); *A61F 2002/30387* (2013.01); *A61F 2002/30398* (2013.01)

(58) Field of Classification Search
CPC ........ A61F 2/4425; A61F 2/443; A61F 2/447; A61F 2/4455
See application file for complete search history.

(56) References Cited

U.S. PATENT DOCUMENTS

| 9,320,610 B2 | 4/2016 | Alheidt et al. |
| 10,342,677 B2 | 7/2019 | Ries |
| 10,507,116 B2 | 12/2019 | Shoshtaev |
| (Continued) |

FOREIGN PATENT DOCUMENTS

| WO | WO2013025876 A1 | 2/2013 |
| WO | WO2014146797 A1 | 9/2014 |
| WO | WO2019169302 A1 | 9/2019 |

OTHER PUBLICATIONS

International Search Report dated Apr. 16, 2021 in corresponding application PCT/EP2021/050788.

*Primary Examiner* — Matthew J Lawson
(74) *Attorney, Agent, or Firm* — Muncy, Geissler, Olds & Lowe, P.C.

(57) ABSTRACT

In an intervertebral implant having at least two upper and two lower contact bodies that have contact surfaces. An actuator has a threaded body which has an extension axis and is provided with opposite-handed threads arranged one behind the other. Wedges sit on the threaded body in an axially moveable manner and can be moved along the threaded body by rotating the same. Ramps of at least one ramp body of a wedge engage at least with counter-surfaces of at least some of the contact bodies and extend toward one another at a finite angle of less than 90°. The wedges are double wedges having two ramp bodies arranged one behind the other, and the ramps of one ramp body are oriented differently to the ramps of the other ramp body. The ramps of the first ramp body engage directly with the contact bodies laterally.

13 Claims, 14 Drawing Sheets

(56) References Cited

U.S. PATENT DOCUMENTS

| | | |
|---|---|---|
| 10,898,344 B2 | 1/2021 | Alheidt et al. |
| 11,285,018 B2 | 3/2022 | Shoshtaev |
| 2017/0333203 A1 | 11/2017 | Glerum et al. |
| 2019/0269521 A1* | 9/2019 | Shoshtaev ............. A61F 2/4455 |
| 2020/0163775 A1* | 5/2020 | Kim ........................ A61F 2/447 |
| 2021/0137695 A1* | 5/2021 | Huang .................. A61F 2/4455 |

* cited by examiner

INTERVERTEBRAL IMPLANT

INTERVERTEBRAL IMPLANT

This nonprovisional application is a continuation of International Application No. PCT/EP2021/050788, which was filed on Jan. 15, 2021, and which claims priority to German Patent Application No. 10 2020 000 319.2, which was filed in Germany on Jan. 21, 2020, and which are both herein incorporated by reference.

BACKGROUND OF THE INVENTION

Field of the Invention

The present invention relates to an intervertebral implant comprising at least two upper and two lower contact bodies that have contact surfaces, comprising an actuator having a threaded body which has an extension axis and is provided with opposite-handed threads arranged one behind the other, and comprising wedges which sit on the threaded body in an axially moveable manner, can be moved along said threaded body by rotating same, and comprise ramps of at least one ramp body of a wedge, which ramps engage at least with counter-surfaces of at least some of the contact bodies and extend toward one another at a finite angle of, for example, less than 90°.

Description of the Background Art

US 2019/0269521 A1 discloses a generic intervertebral implant in which individual contact bodies of the intermediate implant move apart laterally and can be moved apart in the vertical direction. The process of moving laterally apart is achieved, by means of an actuator comprising a threaded rod that has opposite-handed threads, via axially movable sliding bodies which are provided with ramps thereon and engage with corresponding counter-surfaces of the contact bodies.

The process of moving the contact bodies apart vertically is achieved indirectly via intermediate bodies which are arranged between the wedges and the support bodies and can move in obliquely extending grooves of the lower support bodies.

As a result of the intermediate bodies provided as additional movable parts in addition to the wedges and the support bodies, such a configuration is both complex and prone to failure, since it can cause tilting and jamming.

SUMMARY OF THE INVENTION

It is therefore an object of the present invention to provide an intervertebral implant which, while avoiding the aforementioned disadvantages, has a simple structure and ensures reliable functioning while allowing the support bodies to move in different directions in a temporally offset manner.

According to an exemplary embodiment of the invention, this problem is solved by a generic intervertebral implant which is characterized in that the wedges are designed as double wedges having, in a direction of the extension axis, two ramp bodies arranged one behind the other, in that the ramps of one ramp body are oriented differently to the ramps of the other ramp body, and in that the ramps of the first ramp body engage directly with the contact bodies laterally while the ramps of the second ramp body engage directly with the contact bodies in the vertical direction.

The invention therefore provides two ramp bodies which are arranged axially one behind the other and have differently oriented ramps on different ramp bodies on the same double wedge, the first ramp body being used to move the support bodies laterally or sideways apart, and the second ramp body being used to move the support bodies apart in a vertical or cephalocaudal direction.

In particular, the ramps of different orientations are arranged on different ramp bodies of a double wedge.

The ramps of the first ramp bodies can be oriented vertically with a horizontal surface normal, and the surface normals of the ramps of the second ramp bodies, which have a different orientation, include a finite angle other than 90° to the vertical. In a further development, counter-surfaces of the contact bodies that interact with differently oriented ramps and have a different orientation in relation to the spacing of the ramp bodies have a different spacing in the extension direction of the axis of the threaded body of the actuator, in particular the spacing of the differently oriented ramps relative to the spacing of the counter-surfaces on the contact bodies being such that, when the threaded body rotates, the contact bodies are moved apart from one another at least laterally and are only then raised relative to one another.

This can be achieved in that the spacing of the ramps relative to the spacing of the counter-surfaces can be such that the contact bodies first engage laterally with the counter-surfaces of the contact bodies by means of the ramps of the first ramp body in order to move them laterally apart from one another, and only upon further rotation do the ramps of the second ramp body engage with the counter-surfaces of the contact bodies in order to raise them. This specifically achieves a temporally offset movement of the support bodies.

The spacing between the differently oriented ramps of a double wedge having two ramp parts can be less than the spacing between the associated counter-surfaces.

The actuator can have a radial disk rigidly connected to the threaded body or has a radial wheel which engages in slots of the contact bodies that are oriented radially to the axis of the threaded body in order to guide said contact bodies perpendicularly to the axis, and/or guide rods are provided which slidably engage at least in the upper contact bodies and are intended for guiding the contact bodies relative to one another.

The outer contact surface of the upper contact bodies and the lower outer surface of the lower contact bodies do not generally extend parallel to one another; instead, it is preferred that the outer contact surface of the upper contact bodies and the outer contact surface of the lower contact bodies include an angle of between 5° and 15°, preferably between 9° and 11°, in order to achieve better adaptation to the natural lordosis of the lumbar spine. The proximal region of the contact surfaces of each individual contact body, as viewed in relation to the horizontal center plane, first begins with half of this angle linearly increasing surfaces, and then transitions in the distal region into an opposite curvature, in order to form a curve that also facilitates insertion into the intervertebral space.

The ramp bodies on a double wedge can be formed integrally therewith.

Contact bodies above and/or next to one another can be movably connected to one another via linear guides, in particular at least one linear guide being a tongue-and-groove guide, preferably a dovetail guide. As a result of these linear guides, forces occurring under a shear load are conducted through the contact bodies and do not stress, or at least stress to a lesser extent, internal (functional) structures such as the movement mechanism of the double screw.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
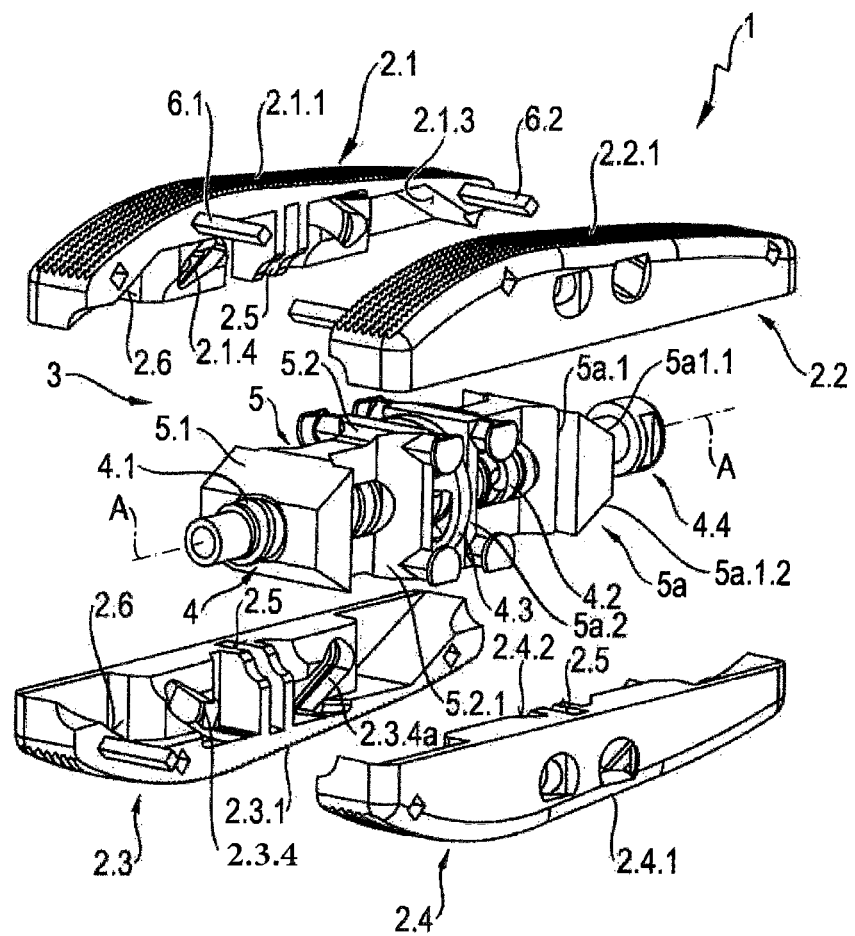
FIG. 1 is an exploded view of a first intervertebral implant according to the invention.

An example of an intervertebral implant according to the invention is shown in FIGS. 1 to FIG. 7a. The implant 1 has two upper contact bodies 2.1 and 2.2 (2.2 is removed in FIGS. 5a, 6a and 7a) and two lower contact bodies 2.3, 2.4 opposite thereto. An actuator or drive mechanism 3 is arranged centrally therebetween (see in particular also FIGS. 3 and 3a).

The contact bodies 2.1-2.4 have contact surfaces which are pointed upward or downward and which, in the central region thereof, for example 2.1.1, 2.2.1, 2.3.1, 2.4.1, are substantially horizontal or form or define a horizontal region, whereas the contact surfaces slope downward or are bent in the longitudinal direction at the ends thereof, and opposing upper and lower contact surfaces thus extend toward one another.

The drive mechanism 3 has a central threaded body 4 having an axis A which also determines the longitudinal direction of the implant. The threaded body 4 has two threads 4.1, 4.2 which are arranged one behind the other and oriented in opposite directions. The thread 4.1 is the distal thread, and the thread 4.2 is the proximal thread. The proximal end of the threaded body 4 is designed to have an engagement contour 4.4 for engaging a tool (not shown) by means of which the threaded body 4 can be rotated. A guide wheel 4.3 is arranged centrally on the threaded body 4 so as to be connected thereto for conjoint rotation, which guide wheel engages in radially oriented transverse slots 2.5 of the contact bodies 2.1-2.4 and thus determines and defines the relative axial position of the contact bodies 2.1-2.4 and of the threaded body 4 relative to one another, independently of the lateral and vertical movements of the contact bodies 2.1-2.4 relative to one another.

Double wedges 5, 5a which have two ramp parts and are provided with internal threads 5.3 adapted to the threads 4.1, 4.2 are seated on the threaded body 4. These double wedges are mirror-symmetrical and are arranged in a mirror-symmetrical manner on either side of the wheel.

Figure 2:
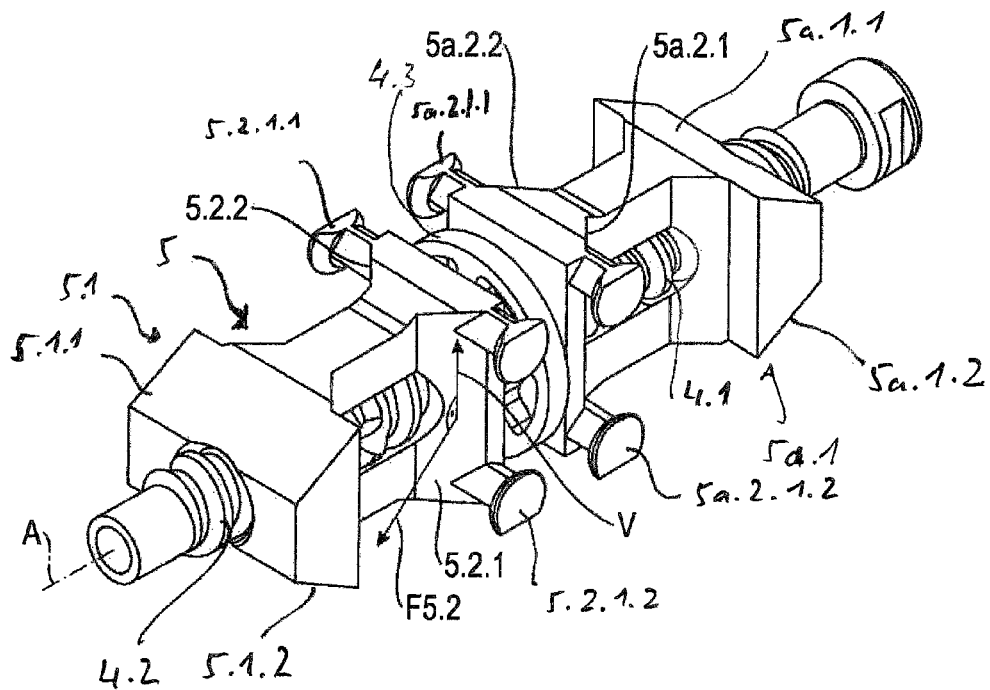
FIG. 2 is a perspective view of the drive mechanism of the implant according to the invention in FIG. 1 in the compressed state.
Figure 2A:
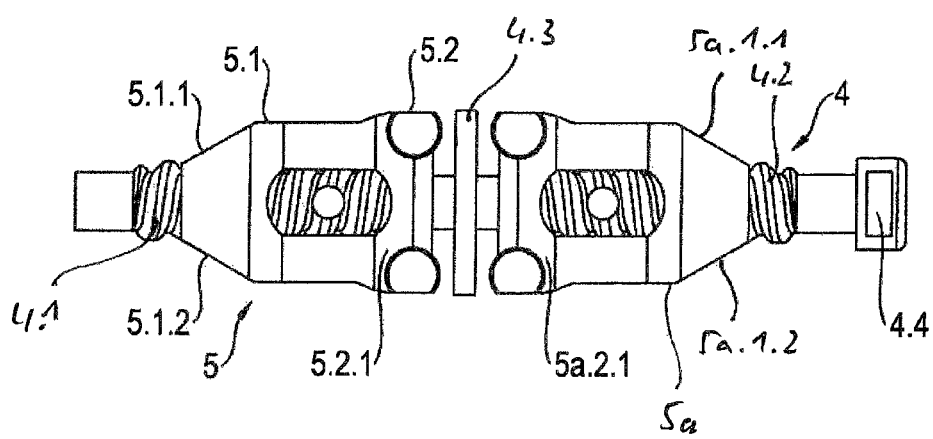
FIG. 2a is a side view of the drive mechanism in FIG. 2.

Each double wedge 5, 5a has a first and a second ramp body 5.1, 5a.1, 5.2, 5a.2, which ramp bodies are each arranged one behind the other in the direction of the axis A and are directed outward away from the wheel 4.3. The ramps 5.1.1 and 5.1.2 of the ramp body 5.1 extend toward one another in an outward direction away from the wheel 4, as follows (FIG. 2): The ramp body 5.1 has, as the upper and lower ramp surface, respectively, a ramp 5.1.1 and 5.1.2 which each have a surface normal F5 having a finite angle other than 90° to a vertical V with respect to the axis A (FIGS. 2 and 2a). The same applies to the other ramps of the ramp body.

The contact body 2.1 (and also the contact body 2.2) has, in relation to the ramp 5.1.1, a counter-surface 2.6 having approximately or exactly the same inclination as the ramps 5.1.1, 5.1.2, against which counter-surface the ramp 5.1.1 or 5.1.2 acts when the double wedge 5 and the ramp body 5.1 and thus the ramps 5.1.1, 5.1.2 are moved outward away from the wheel 4.3 along the axis A (in the figure to the left) while the threaded body 4 rotates.

The same applies in principle to the ramp body 5*a*.1 and the ramps 5*a*.1.1, 5*a*.1.2 located thereon, with the corresponding counter-surface 2.1.3 being formed on the inside of the contact body 2.1. The same applies to the corresponding ramps of the contact body 2.2, and to the lower ramp 5*a*.1.2 and corresponding counter-surfaces of the lower contact bodies 2.3 and 2.4.

Figure 3:
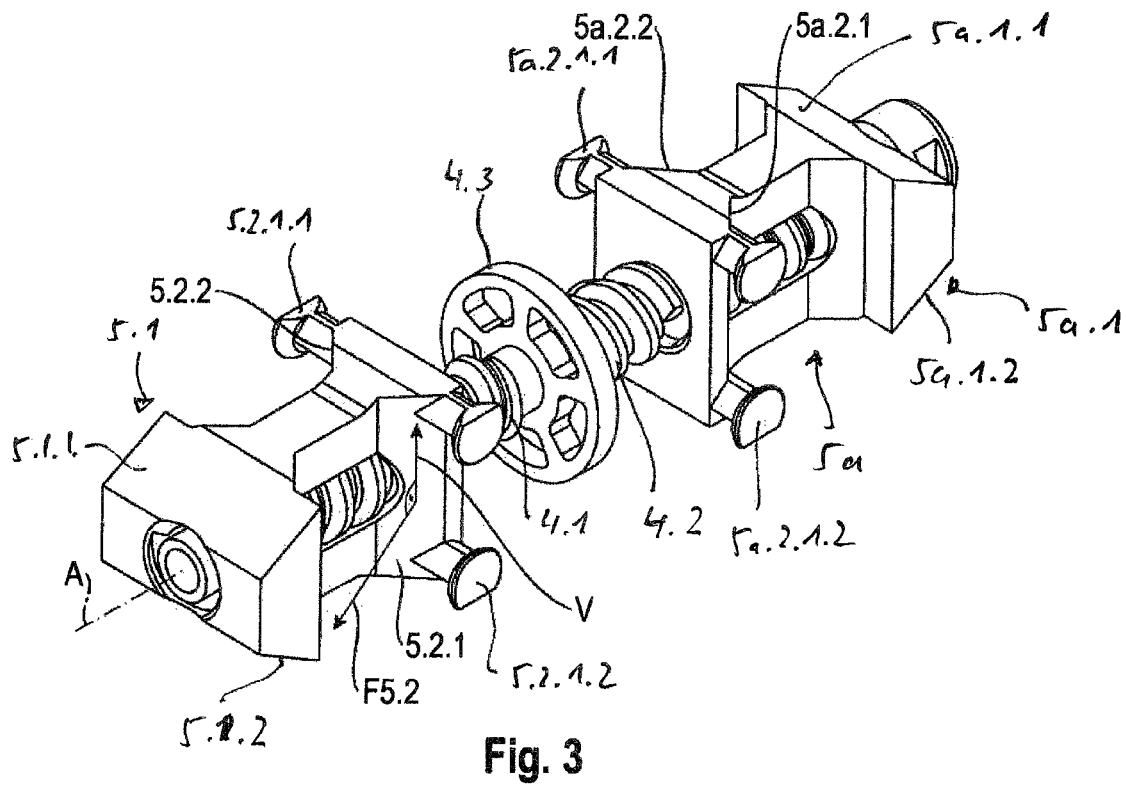
FIG. 3 is a perspective view of the drive mechanism of the embodiment in FIG. 1 in the expanded state.
Figure 3A:
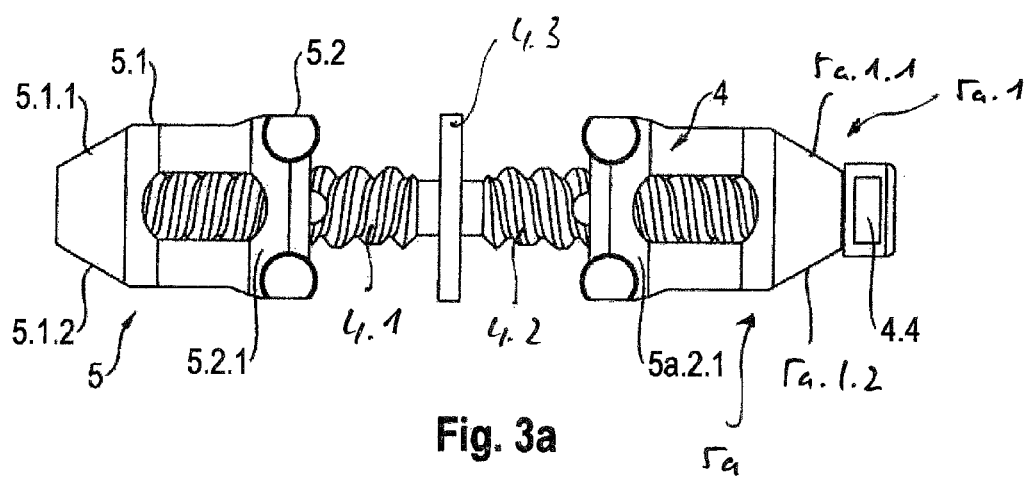
FIG. 3a is a side view of the drive mechanism according to FIG. 3.
Figure 4:
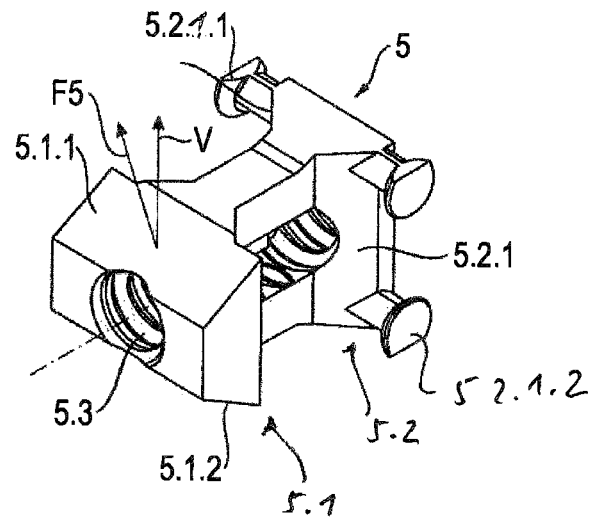
FIG. 4 is a perspective view of a double wedge of the implant according to the invention in FIG. 1.
Figure 4A:
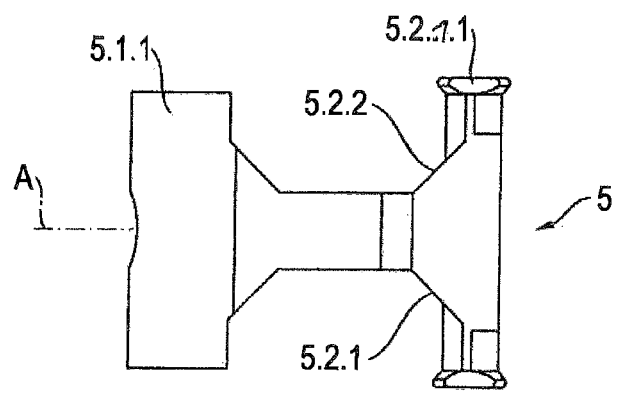
FIG. 4a is a plan view of the double wedge in FIG. 4.
Figure 4B:
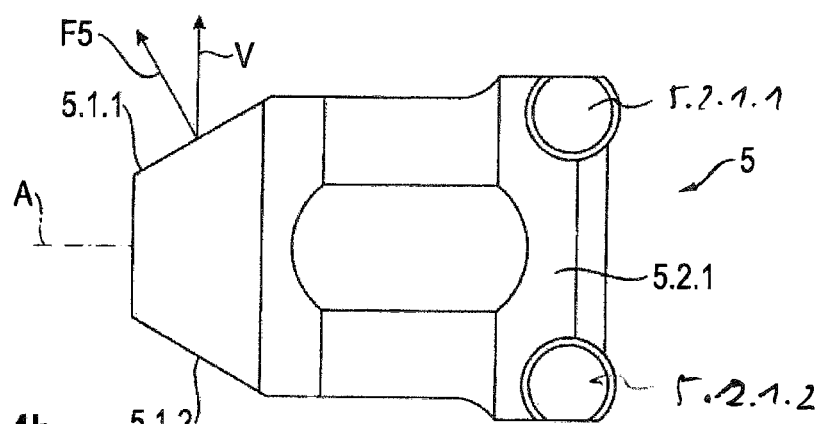
FIG. 4b is a side view of the double wedge in FIG. 4.

As stated, the double wedge 5 has, inwardly offset from the ramp body 5.1 in the axis direction A, the ramp body 5.2 which comprises the ramps 5.2.1 and 5.2.2 that are oriented vertically (see also FIG. 3), also extend obliquely toward one another in an outward direction from the wheel 4.3 and each have a surface normal F5.2 which is oriented horizontally, i.e. perpendicularly to the vertical V, and spans a horizontal plane with the axis A (FIG. 3).

The ramp 5.2.1 interacts with a counter-surface 2.4.2 on the contact body 2.4 that is also vertically aligned and extends obliquely, and also with a corresponding counter-surface on the front upper contact body 2.3, and can, when the double wedge 5 is moved outward from the wheel 4.3 as a result of the threaded body 4 rotating, move the contact body 2.4 (and also the contact body 2.3) outward until the ramp 5.2.1 disengages from the counter-surface 2.4.2 (and the corresponding counter-surface of the contact body 2.3), such that, with a further screwing movement of the threaded body 4, the double wedge 5 can then move along the contact body 2.4 and also the contact body 2.3.

The same applies to the ramp 5.2.2 and the corresponding counter-surface on the contact bodies 2.1 and 2.2, and the corresponding ramps 5*a*.2.1, 5*a*.2.2 of the ramp body 5*a*.2 on the double wedge 5*a* (FIGS. 3 and 3*a*), with reference being made to the above explanation regarding the interaction of the ramp 5.2.1 and the counter-surface 2.4.2.

In the first embodiment in FIG. 1-7*a*, the ramp body 5.2 has upper and lower lugs 5.2.1.2 (FIG. 2) extending laterally away therefrom and beyond the ramps 5.2.1; said lower lug engages in a slot 2.1.4 of the contact body 2.1 and thus guides it horizontally when the contact bodies move laterally apart as a result of the contact surfaces of the ramp bodies 5.2 relative to one another. The same applies to the second lugs of the ramp bodies 5.2 and 5*a*.2 and associated slots 2.3.4 of the contact bodies 2.1-2.4.

The slot 2.1.4, in the region thereof directed toward the end faces, has edges bent toward one another. This ensures guidance when the contact bodies 2.1 and 2.3 or also 2.2 and 2.4 move apart from one another in the vertical direction under the action of the ramp bodies 5.1, 5*a*.1, as has been described above.

The same applies to the lugs (shown in the drawings) in the region of the ramp body 5*a*.2 and associated slots such as 2.3.4*a*., with reference also being made to the above description in this respect and in relation to corresponding lugs on the opposite side of said two ramp bodies and to corresponding slots in the contact bodies 2.1 and 2.2.

Lastly, guide rods 6.1, 6.2 are formed between the contact bodies 2.1 and 2.2, which guide rods can move in the two contact bodies 2.1, 2.2 and guide the two contact bodies relative to one another during their lateral movement apart and vertical lifting movement.

Corresponding guide rods are provided in the lower contact bodies 2.3 and 2.4, which guide rods also guide these bodies toward one another during said lateral movement and a lowering movement.

The figures, in particular FIG. 1, show that the axial spacing from the ramp body 5.2 and thus the ramp 5.2.1 thereof to the ramp body 5.1 and the ramp 5.1.1 thereof (and the corresponding ramps that are not shown) is less than the axial spacing between the counter-surface 2.4.2 and the counter-surface 2.6 or the corresponding counter-surface of the same contact body. The same applies to the spacing of the ramp bodies 5*a*.2 and 5*a*.1 and the ramps thereof in relation to the corresponding counter-surfaces on the contact bodies.

This ensures that both the upper contact bodies 2.1 and 2.2 and the lower contact bodies 2.3 and 2.4 are initially, in a first step, moved apart laterally by the ramp bodies 5.2 and 5*a*.2 and the ramps thereof and only then, i.e. offset in time from the aforementioned step, are the contact bodies 2.1 and 2.3 and the contact bodies 2.2 and 2.4 moved apart by the ramp bodies 5.1 and 5*a*.1 and the ramps in the perpendicular or vertical direction; it is therefore only in the laterally widened state that the contact bodies 2.1-2.4 are moved against the upper and lower vertebrae, thereby reducing the risk of damage to said vertebrae.

An exemplary intervertebral implant according to the invention is shown in FIGS. 8 to 11*a*. This embodiment has, in principle, largely the same configuration as the first embodiment in FIGS. 1 to 7*a*. In this respect, identical parts are provided with the same reference signs and, for the description of said parts, reference is made to the above description of the first embodiment. The main difference from the somewhat different configuration of the ramp bodies 5.2, 5.2*a* is the double wedge 5, 5*a*. The difference is that, instead of the two-sided lugs of the corresponding ramp body in the embodiment in FIGS. 1 to 7*a*, these have, on each side, a lateral lug 5.2.5 and 5.2.6 of the ramp body 5.2 and 5*a*.2.6 of the ramp body 5*a*.2 (the lug provided on the other side of the ramp body 5*a*.2 is not shown in the drawings). The lugs 5.2.5, 5.2.6 and 5*a*.2.6 are arranged at mid-height of the ramp body 5.2 or 5*a*.2. Said lugs engage in slots 2.1.5, 2.1.6, 2.2.5, 2.2.6, 2.3.5, 2.3.6, 2.4.5, 2.4.6, which extend first horizontally and then obliquely; the outer inclined portion of the slots 2.1.5, 2.1.6, 2.2.5, 2.2.6 of the upper contact bodies 2.1, 2.2 extends downward and outward, while the outer inclined portions of the slots 2.3.5, 2.3.6, 2.4.5, 2.4.6 of the lower contact bodies 2.3, 2.4 extend outward and upward.

This has the effect that, when the lugs 5.2.5 and 5.2.6 (and the corresponding lugs of the ramp body 5*a*) enter the inclined portions of said slots, the lower contact bodies 2.3 and 2.4 are pushed downward and the upper contact bodies 2.1 and 2.2 are pushed upward, thus producing a vertical spread. The preceding horizontal spreading of the contact bodies 2.1 and 2.2 relative to one another and 2.3 and 2.4 relative to one another takes place in the same way as described with reference to the first embodiment.

Figure 10:
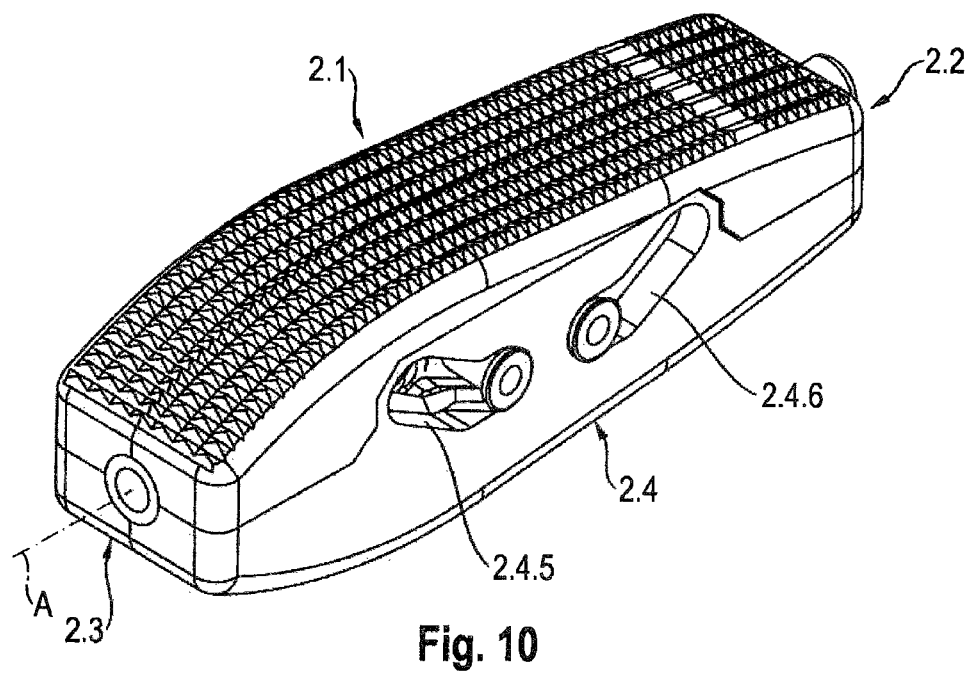
FIG. 10 is a perspective view of the implant in FIG. 8 in the compressed state.
Figure 10A:
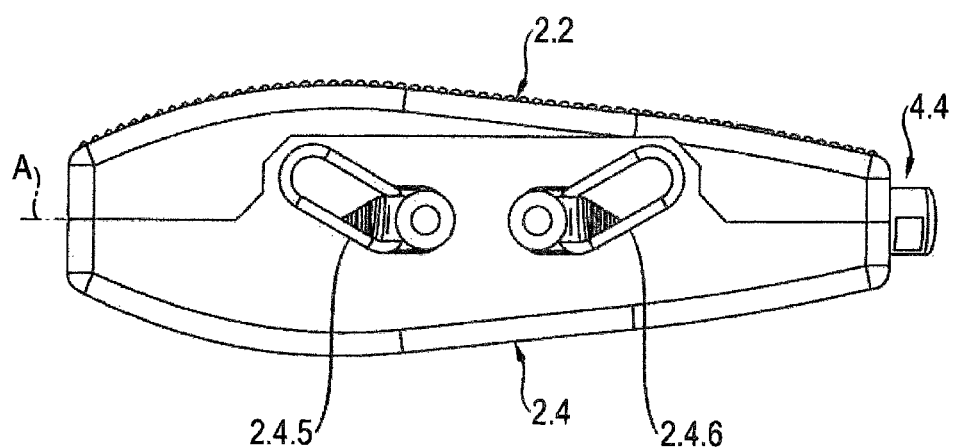
FIG. 10a is a side view of the implant in FIGS. 8 and 10 in the compressed state.
Figure 11:
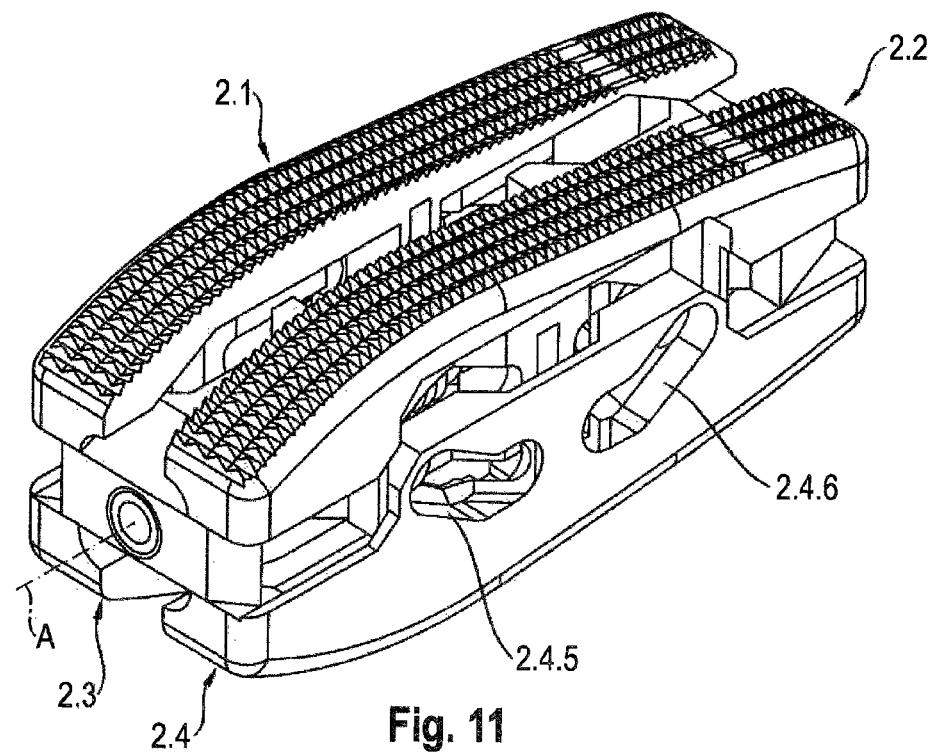
FIG. 11 is an exploded view of an implant in FIG. 8 in the fully expanded state.
Figure 11A:
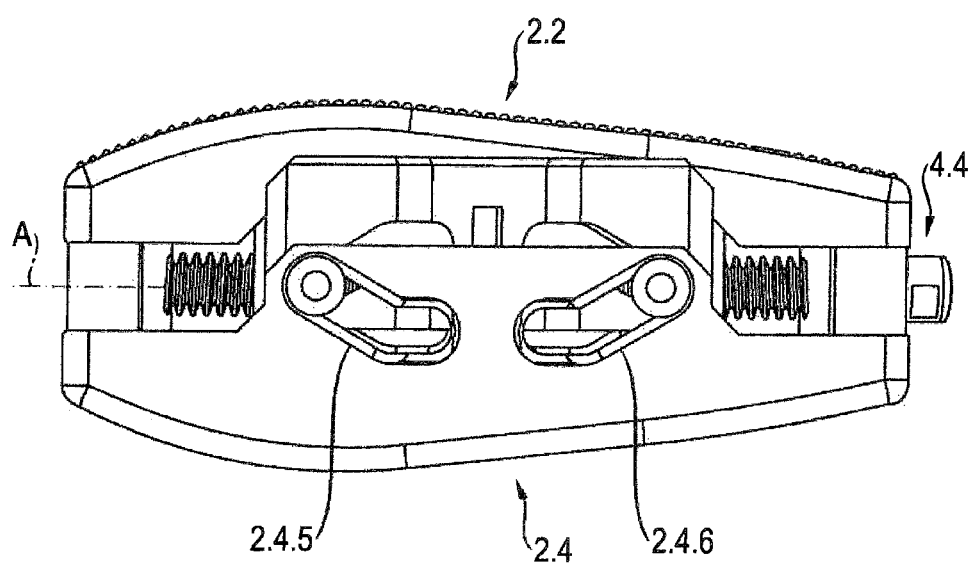
FIG. 11a is a side view of the implant in FIG. 8 in the fully expanded state.

In order for the lugs 5.2.5 and 5.2.6 as well as 5*a*.2.6 (and the corresponding opposite lug of the ramp body 5*a*.2) to each be able to engage simultaneously in a slot in a lower contact body and in an upper contact body, in order to move the corresponding vertical spreads, i.e. for example the lug 5.2.5 both in the slot 2.3.5 of the contact body 2.3 and in the slot 2.1.5 of the contact body 2.1, the slots must overlap when in the compressed basic configuration (FIGS. 10 and 10*a*). Accordingly, a horizontal region 2.1.7, 2.2.7 comprising the slots 2.1.5, 2.1.6 or 2.2.5, 2.2.6 engages, in the vertical direction, inside a side wall of the corresponding lower contact body 2.3 or 2.4, as a result of which the slots overlap in their horizontal region, as can be readily seen by conceptually bringing the contact bodies 2.1 and 2.3 and the contact bodies 2.2 and 2.4 in FIG. 8 together.

Figure 12:
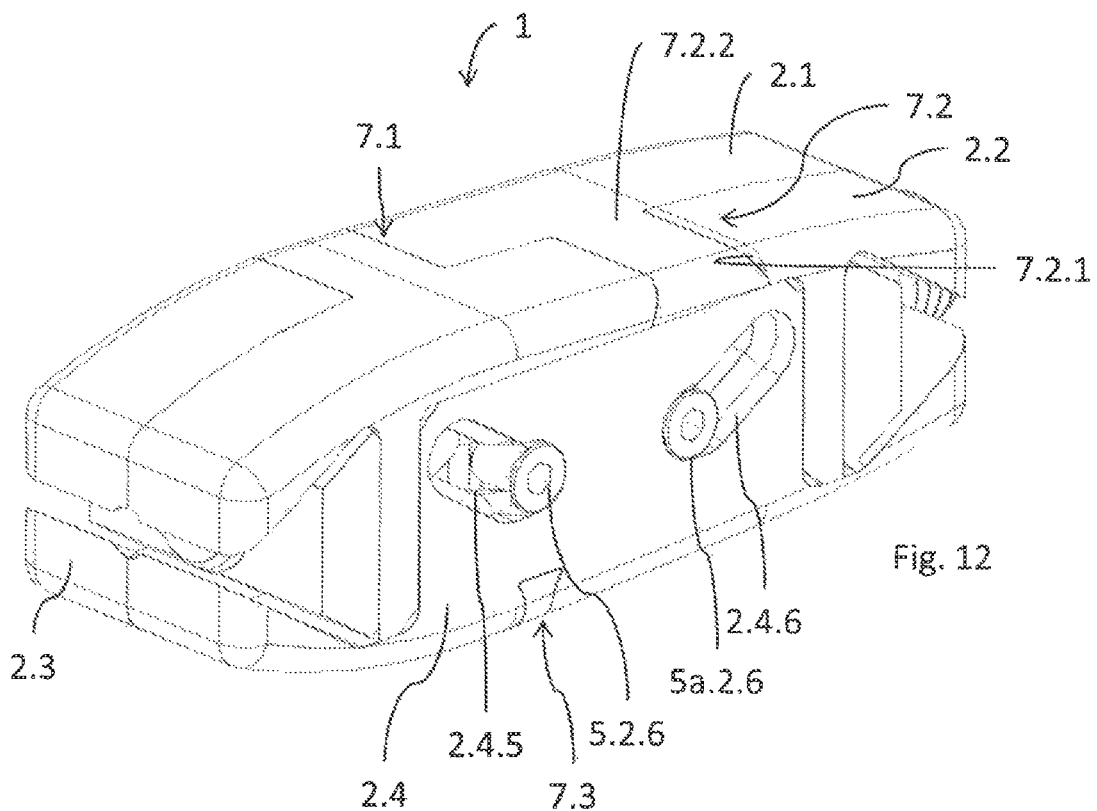
FIG. 12 shows a modified embodiment of the intervertebral implant according to the invention with linear guides in the compressed state.
Figure 13:
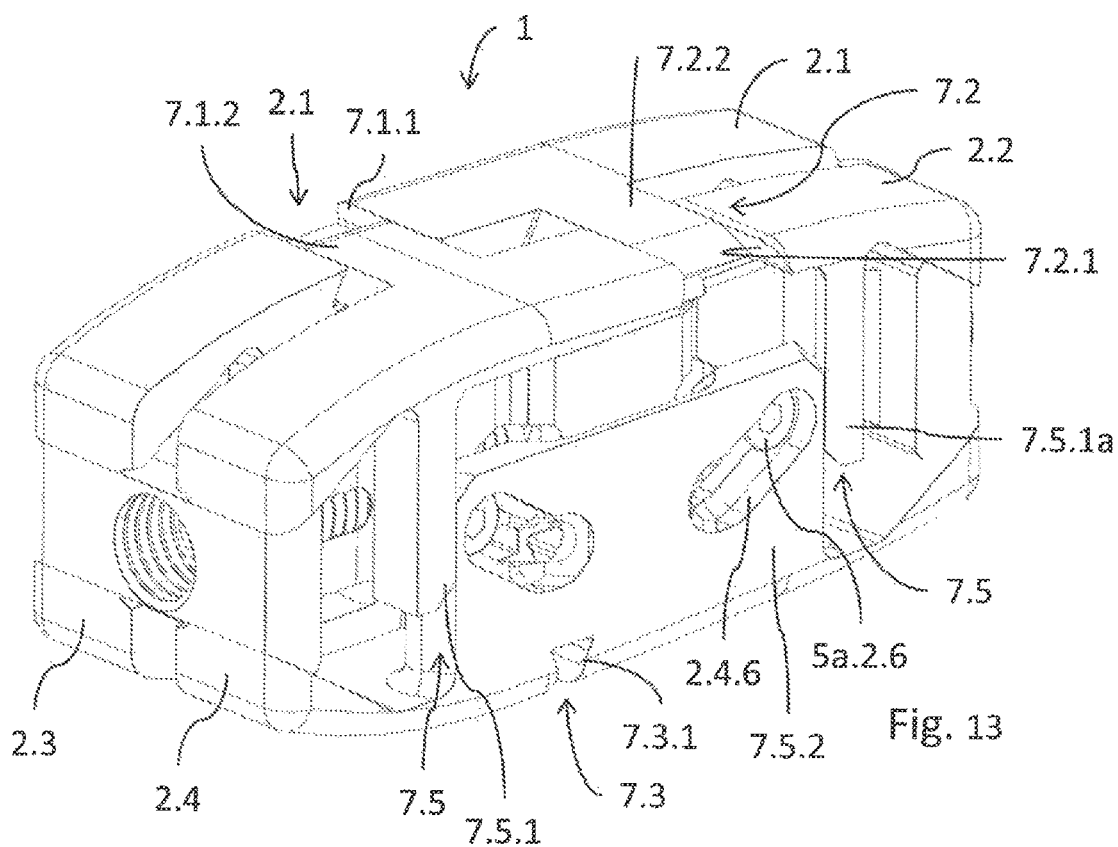
FIG. 13 shows the embodiment in FIG. 12 in a laterally or horizontally expanded state.
Figure 14:
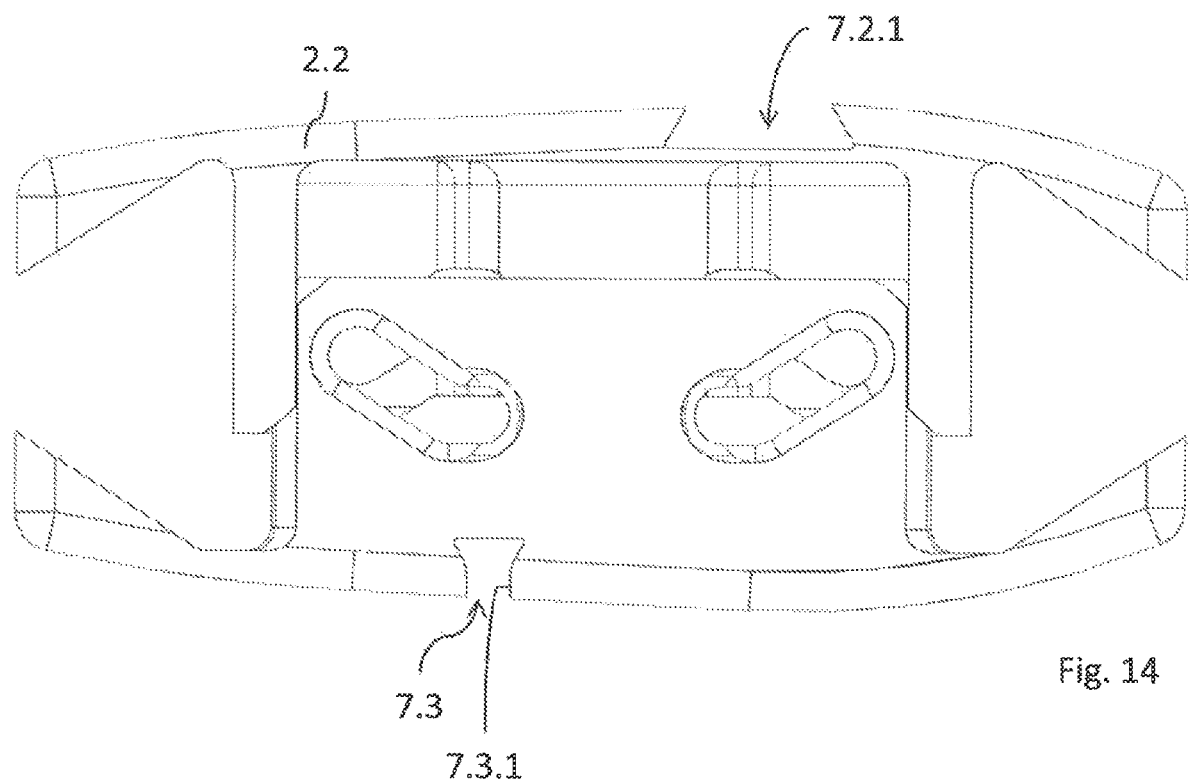
FIG. 14 is a side view of the intervertebral implant according to the invention in FIG. 12 in the region of the right-hand upper and lower contact bodies, as seen from the engagement side.

FIGS. 12 to 16 show a further modification to the intervertebral implant in the previous figures. Identical parts are denoted by the same reference signs. The intervertebral implant in FIGS. 12 to 16 also has upper contact bodies 2.1, 2.2 and lower contact bodies 2.3, 2.4. FIG. 12 shows the intervertebral implant 1 in the compressed state, and FIG. 13 shows the intervertebral implant in an only laterally or horizontally expanded state.

Firstly, the implant 1 has linear guides 7.1, 7.2 for the two upper contact bodies 2.1, 2.2 (FIGS. 12 and 13). It also has linear guides 7.3, 7.4 for the two lower contact bodies 2.3, 2.4 (FIGS. 12, 13, 14 and 16). The linear guides 7.1-7.4 are used for laterally or horizontally guiding the upper contact bodies 2.1, 2.2 or the lower contact bodies 2.3, 2.4 toward one another. Corresponding vertical linear guides for the contact bodies 2.1 and 2.3 or 2.2 and 2.4 located directly above one another are also provided; the drawings, more precisely FIG. 13, only show a vertical linear guide 7.5 for the contact bodies 2.2, 2.4, which will be explained further below.

Figure 15:
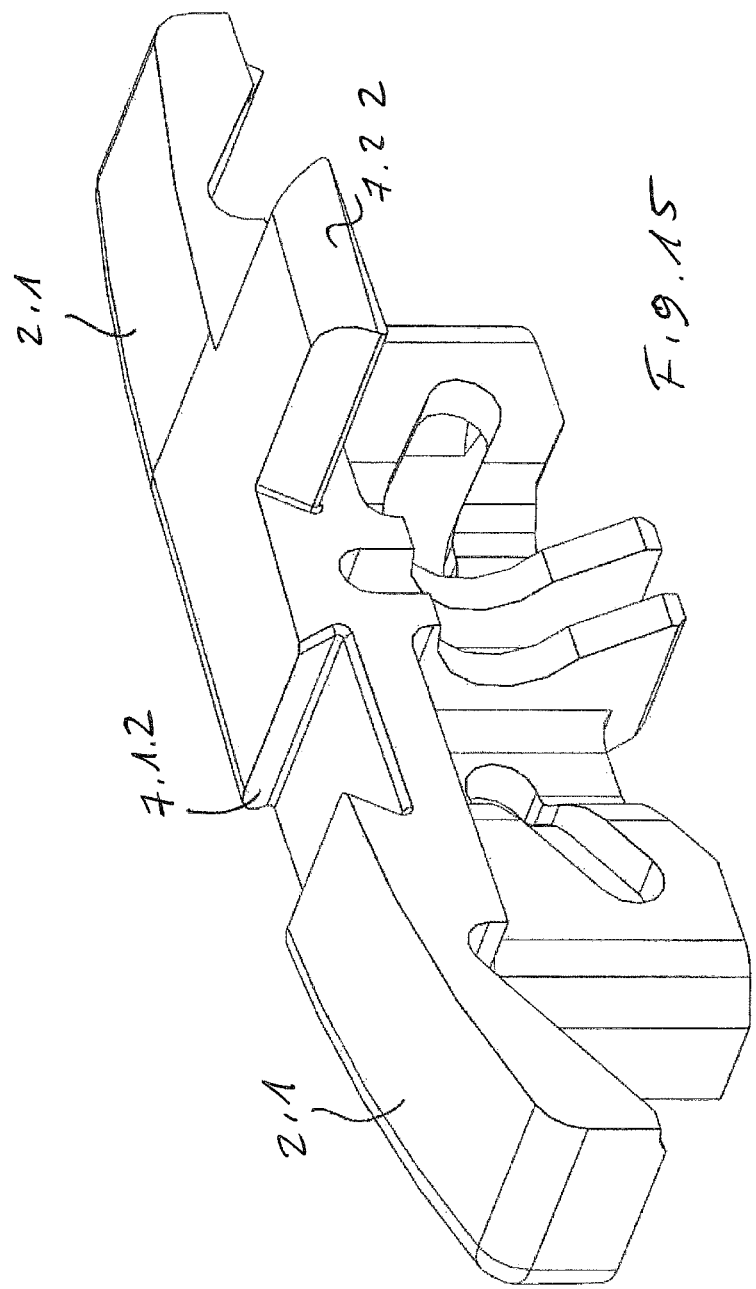
FIG. 15 is a perspective view of the inside of the left-hand upper contact body, as seen from the engagement side.
Figure 16:
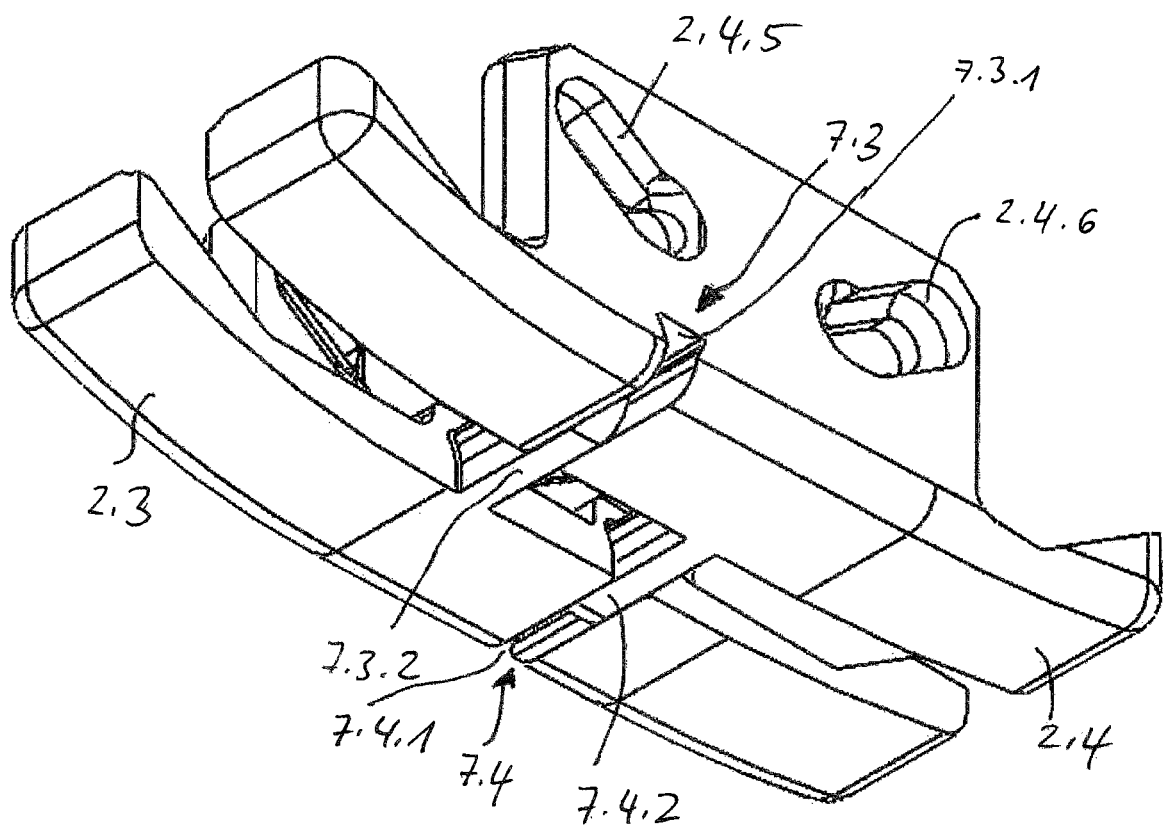
FIG. 16 is a view from below of adjacent lower contact bodies.

Each linear guide 7.1-7.2 can be formed of a tongue-and-groove guide, in particular a dovetail guide comprising undercuts; the latter is the case and can be seen in the guide 7.3 in FIGS. 12, 13 and 16 and the guides 7.1 and 7.2 in FIGS. 13 and 15. The same applies to the guide 7.5 in FIG. 13.

Accordingly, each linear guide can have a groove and a projection or lug, usually referred to as a "tongue," which engages in this groove. In the linear guide 7.1, these are the groove 7.1.1 and the tongue 7.1.2; in the linear guide 7.2, these are the groove 7.2.1 and the tongue or the projection 7.2.2 (see in particular FIG. 13). In the linear guide 7.3, these are the groove 7.3.1 and the tongue 7.3.2; in the linear guide 7.4, these are the groove 7.4.1 and the tongue 7.4.2 (FIG. 16).

In the vertical linear guide 7.5 which is shown in FIG. 13, the groove is formed between the two guide projections 7.5.1 and 7.5.1a which lead downward, and the corresponding tongue or the projection of the guide 7.5 is formed by the side wall 7.5.2 of the right-hand lower support body, as seen from the engagement side. The mutually interacting side walls of the projection or the tongue 7.5.2 and the guide projections 7.5.1, 7.5.1a are also dovetail-shaped with undercuts, as can be seen in FIG. 13.

A vertical linear guide for the support bodies 2.1, 2.3 located above one another is designed in the same way as the linear guide 7.5.

The linear guides ensure that transverse forces that occur are absorbed by said guides and, in particular, that the double screw 4 and the threads of the wedge bodies that interact with said screw are freed from such forces or at least relieved therefrom.

The intervertebral implant 1 according to the invention can be, for example, introduced and positioned in the following manner:

First, access to the intervertebral space is established, as is described, for example, in WO 2014/146797, which corresponds to US 2016/0045334, which are herein incorporated by reference.

Figure 5:
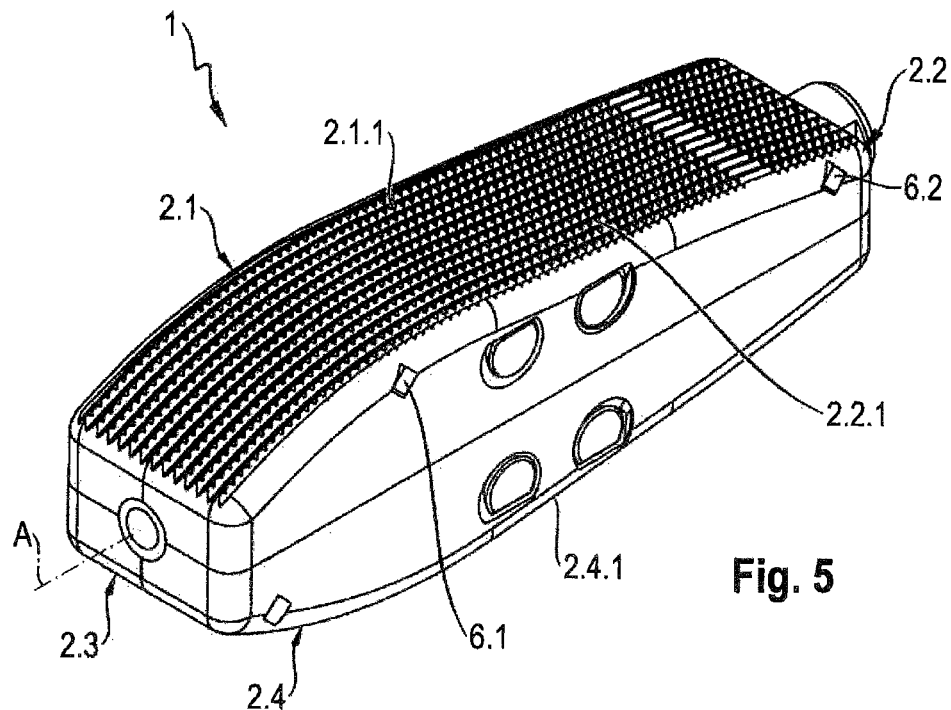
FIG. 5 shows the complete implant in a compressed state.
Figure 5A:
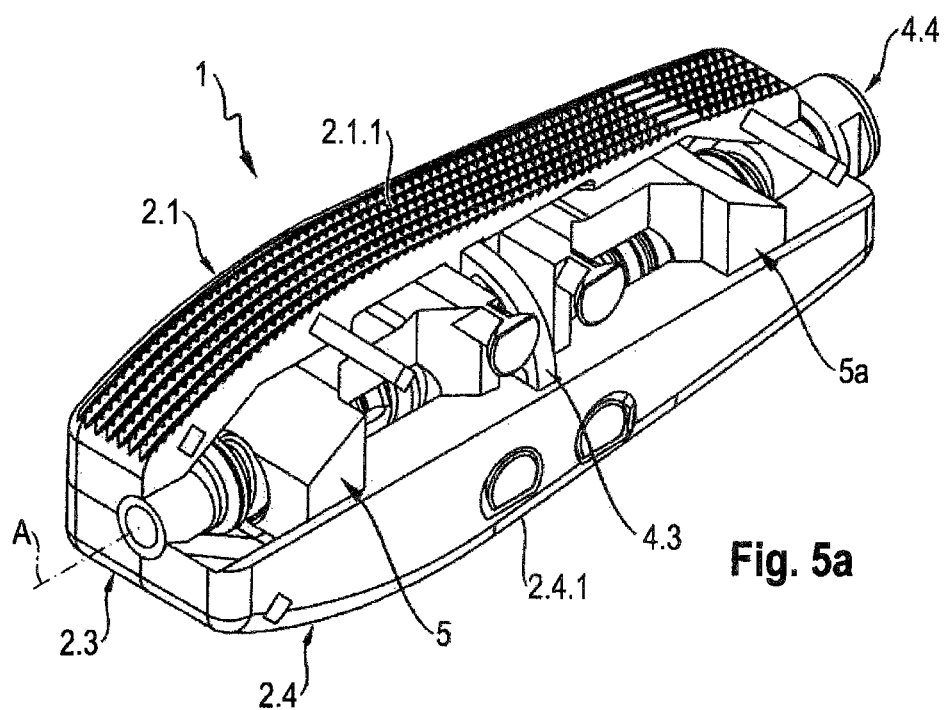
FIG. 5a shows the implant in the compressed state, with the upper front contact body removed.
Figure 6:
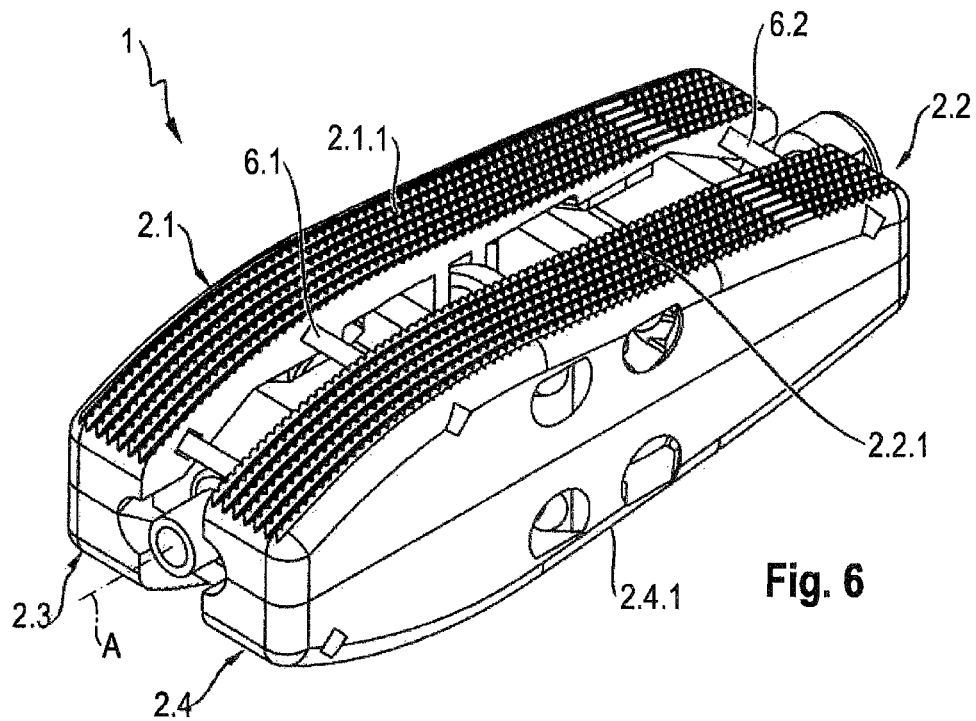
FIG. 6 shows the implant according to a first step in an only laterally expanded state.
Figure 6A:
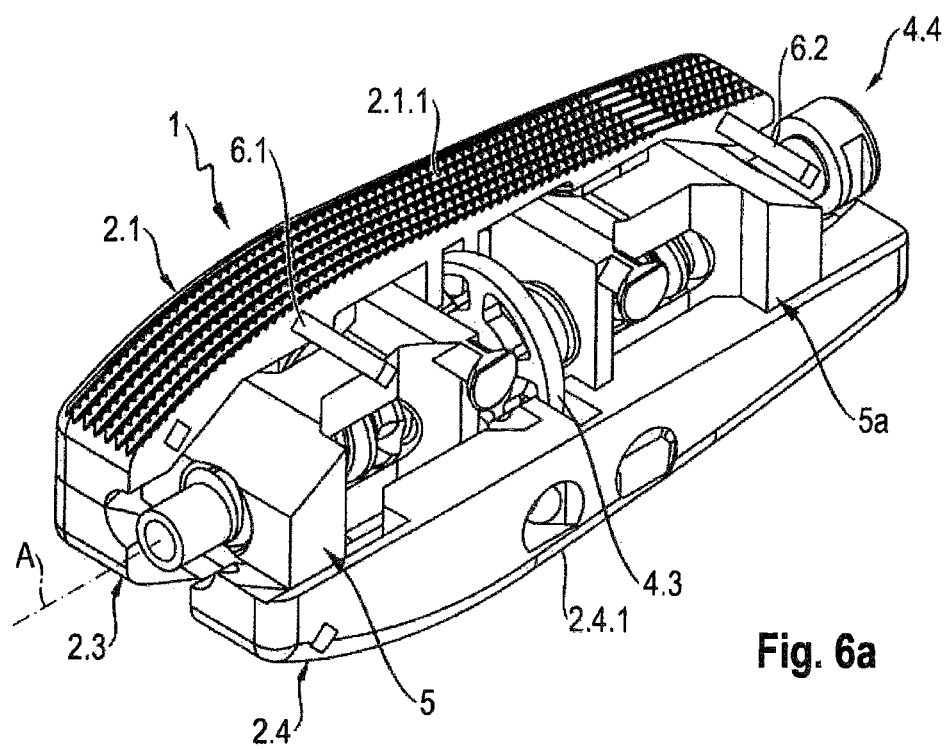
FIG. 6a shows the implant according to a first step in the only laterally expanded state according to FIG. 6, with the upper front contact body removed.

The intervertebral implant 1, in its compressed state according to the configuration in FIG. 5, is then inserted through the access sleeve. In so doing, the intermediate configuration in FIGS. 6 and 6a is achieved. When the intervertebral implant 1 has reached its position between the two vertebrae, specifically a vertebra located below said implant and a vertebra located above, a tool is used, through the insertion sleeve, to grip an actuating part at the proximal end of the intervertebral implant 1, and the threaded body 4 is rotated using the tool. Since the two double wedges 5, 5a cannot rotate together, they are moved from the starting position in opposite directions away from one another as a result of the threaded connection between them and the opposite-handed external threads of the threaded body, as can be seen in the transition from FIG. 2 to FIG. 3.

Figure 7:
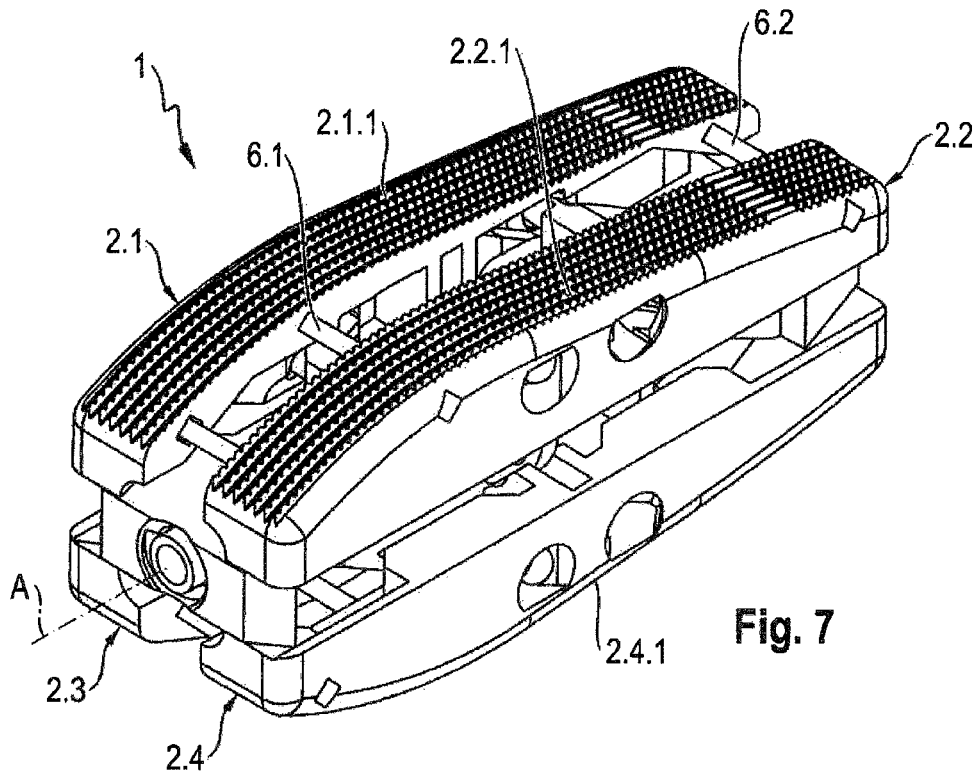
FIG. 7 shows the implant according to the invention in the laterally and vertically expanded state after the second expansion step.
Figure 7A:
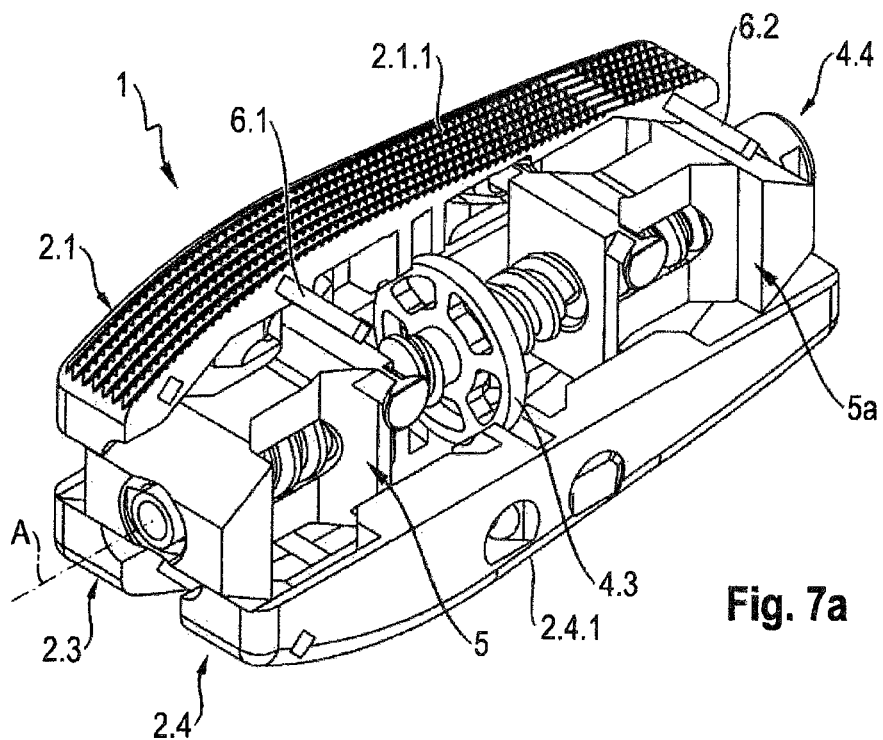
FIG. 7a shows the implant according to the invention in the laterally and vertically expanded state after the second expansion step according to FIG. 7, with the upper front support body removed.
Figure 8:
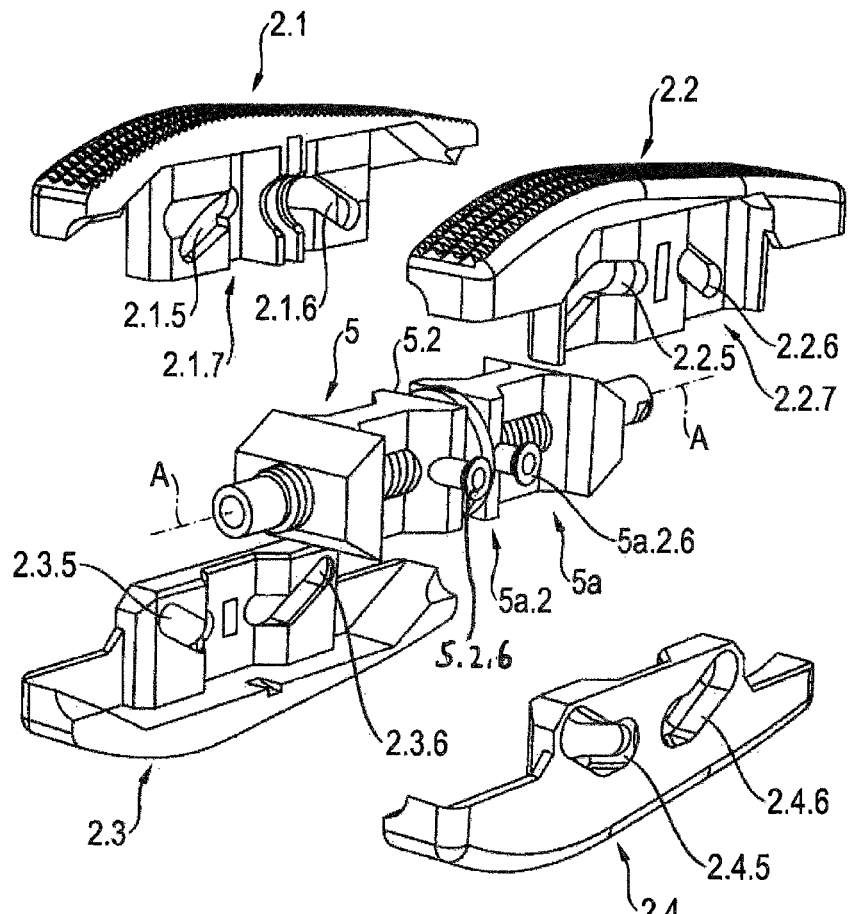
FIG. 8 is an exploded view of a different embodiment of the intervertebral implant according to the invention.
Figure 9:
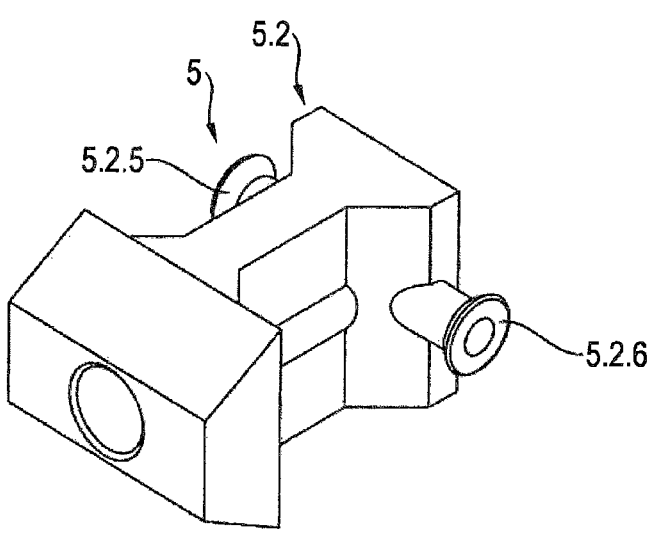
FIG. 9 is a perspective view of a different double wedge of the embodiment in FIG. 8.

First, the ramp bodies 5.2 and 5a.2 engage with the corresponding counter-surfaces of the contact bodies 2.1-2.4 and move them laterally apart from one another until the counter-surface of the contact bodies, for example 2.4.2, releases the corresponding ramp such that it can be moved along the support body upon further rotation of the threaded body 4. At the same time, i.e. after the support bodies have been moved completely laterally apart, the ramps of the ramp body 5.1 engage with the corresponding counter-surfaces, such as 2.6, of the contact bodies, such that when the threaded body is rotated further, they are raised by means of the two mentioned surfaces until the configuration in FIGS. 7 and 7a is reached.

In this last method step, the contact bodies are moved so as to have their outer lateral surfaces against the vertebrae, thus at least bracing the vertebrae and the intervertebral implant.

Because the contact bodies only move against the vertebrae in the laterally spread state, the risk of damage to the vertebrae is significantly reduced or eliminated.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An intervertebral implant comprising:
   at least two upper and two lower contact bodies having contact surfaces;
   an actuator having a threaded body that has an extension axis and is provided with opposite-handed threads arranged one behind the other;
   at least two wedges arranged on the threaded body in an axially moveable manner that are adapted to be moved along the threaded body by rotating; and
   at least two ramps of at least one ramp body of a wedge, the at least two ramps engaging at least with counter-surfaces of at least a portion of the contact bodies and extend toward one another at a finite angle of less than 90°,
   wherein the wedges are designed as double wedges having, in a direction of the extension axis, two ramp bodies arranged one behind the other,
   wherein the at least two ramps of one ramp body are oriented differently to the ramps of the other ramp body, and
   wherein ramps of a first ramp body engage directly with the contact bodies laterally, and ramps of a second ramp body engage directly with the contact bodies in the vertical direction.

2. The intervertebral implant according to claim 1, wherein the ramps of the first ramp bodies are oriented vertically, such that the ramps of the first ramp bodies have a horizontal surface normal, and wherein the ramps of the second ramp bodies are oriented differently than the ramps of the first ramp bodies, such that surface normals of the ramps of the second ramp bodies have a finite angle other than 90° to the vertical.

3. The intervertebral implant according to claim 1, wherein the ramps of different orientations are arranged on different ramp bodies.

4. The intervertebral implant according to claim 1, wherein counter-surfaces of the contact bodies, which interact with differently oriented ramps, have a different orientation in relation to the spacing of the ramp bodies and have a different spacing in the extension direction of the axis of the threaded body of the actuator.

5. The intervertebral implant according to claim 1, wherein the spacing of the differently oriented ramps relative to the spacing of the counter-surfaces on the contact bodies is such that, when the threaded body rotates, the contact bodies are moved apart from one another at least laterally and are only then raised relative to one another.

6. The intervertebral implant according to claim 1, wherein the spacing of the ramps relative to the spacing of the counter-surfaces is such that the contact bodies first engage laterally with the counter-surfaces of the contact bodies via the ramps of the first ramp body in order to move them laterally apart from one another, and only upon further rotation do the ramps of the second ramp body engage with the counter-surfaces of the contact bodies in order to raise them.

7. The intervertebral implant according to claim 1, wherein a spacing between the differently oriented ramps of a double wedge is less than a spacing between the associated counter-surfaces.

8. The intervertebral implant according to claim 1, wherein the actuator has a radial disk rigidly connected to the threaded body or has a radial wheel which engages in slots of the contact bodies that are oriented radially to the axis of the threaded body in order to guide the contact bodies substantially perpendicularly to the axis.

9. The intervertebral implant according to claim 1, further comprising at least two guide rods that slidably engage at least in the upper contact bodies and are intended for guiding the contact bodies relative to one another.

10. The intervertebral implant according to claim 1, wherein an outer contact surface of the upper contact bodies and an outer contact surface of the lower contact bodies include an angle of between 5° and 15° or between 9° and 11°.

11. The intervertebral implant according to claim 1, wherein the ramp bodies on a double wedge are formed integrally therewith.

12. The intervertebral implant according to claim 1, wherein contact bodies above and/or next to one another are movably connected to one another via linear guides.

13. The intervertebral implant according to claim 12, wherein at least one linear guide is a tongue-and-groove guide or a dovetail guide.

\* \* \* \* \*